(12) United States Patent
Dreyer et al.

(10) Patent No.: US 10,955,404 B2
(45) Date of Patent: Mar. 23, 2021

(54) INTEGRATED CIRCUITS FOR ANALYZING BIOLOGICAL SYSTEMS

(71) Applicant: AXBIO INC., Santa Clara, CA (US)

(72) Inventors: Stephen F. Dreyer, Santa Clara, CA (US); Priyanka Agrawal, Santa Clara, CA (US); Hui Tian, Santa Clara, CA (US)

(73) Assignee: AXBIO INC., Santa Clara, CA (US)

( * ) Notice: Subject to any disclaimer, the term of this patent is extended or adjusted under 35 U.S.C. 154(b) by 152 days.

(21) Appl. No.: 16/420,585

(22) Filed: May 23, 2019

(65) Prior Publication Data

US 2019/0360996 A1 Nov. 28, 2019

Related U.S. Application Data

(60) Provisional application No. 62/675,517, filed on May 23, 2018.

(51) Int. Cl.
*C12M 3/00* (2006.01)
*G01N 33/00* (2006.01)
*G01N 33/483* (2006.01)
*C12M 1/34* (2006.01)

(52) U.S. Cl.
CPC ......... *G01N 33/4836* (2013.01); *C12M 41/46* (2013.01)

(58) Field of Classification Search
CPC ........... G01N 33/4836; G01N 27/3276; G01N 27/27; C12M 41/46; B01L 3/502715
See application file for complete search history.

(56) References Cited

U.S. PATENT DOCUMENTS

| | | | |
|---|---|---|---|
| 5,815,690 A * | 9/1998 | Kowert | H04J 3/062 702/190 |
| 6,485,690 B1 | 11/2002 | Pfost et al. | |
| 8,741,117 B2 | 6/2014 | Daniels et al. | |
| 2001/0026778 A1* | 10/2001 | Ackley | B01L 3/5027 422/129 |
| 2009/0167288 A1 | 7/2009 | Reid et al. | |
| 2012/0024700 A1 | 2/2012 | Boccardi et al. | |
| 2012/0028845 A1 | 2/2012 | Teggatz et al. | |
| 2012/0064567 A1* | 3/2012 | Stakenborg | G01N 15/1209 435/39 |
| 2012/0267729 A1 | 10/2012 | Dang et al. | |
| 2013/0260472 A1 | 10/2013 | Holt | |
| 2013/0345065 A1 | 12/2013 | Hasibi et al. | |
| 2014/0110259 A1 | 4/2014 | Takahashi et al. | |
| 2014/0318958 A1 | 10/2014 | Hassibi et al. | |
| 2015/0125872 A1 | 5/2015 | Chen et al. | |

(Continued)

FOREIGN PATENT DOCUMENTS

WO 2016/154302 A1 9/2016

OTHER PUBLICATIONS

International Search Report and Written Opinion for Application No. PCT/US2019/033708, dated Sep. 5, 2019, 14 pages.

(Continued)

*Primary Examiner* — Nathan A Bowers (57) ABSTRACT

Integrated circuits for sensing biological molecules are disclosed. The integrated circuits can be used to measure the impedance of a biological sample under test. The integrated circuits can be used to sequence polynucleotides using a cell array.

22 Claims, 2 Drawing Sheets

(56) References Cited

U.S. PATENT DOCUMENTS

2015/0275287 A1 10/2015 Tian
2016/0370313 A1 12/2016 Aparin

OTHER PUBLICATIONS

Non-Final Office Action for U.S. Appl. No. 15/628,517, dated Jul. 17, 2018, 10 pages.
Final Office Action for U.S. Appl. No. 15/628,517, dated Jan. 15, 2019, 12 pages.
International Search Report for Application No. PCT/US2017/038376, dated Sep. 19, 2017, 10 pages.
International Search Report and Written Opinion for Application No. PCT/US2017/038376, dated Nov. 9, 2017, 16 pages.
International Preliminary Report on Patentability for Application No. PCT/US2017/038376, dated Jan. 3, 2019, 9 pages.
International Search Report and Written Opinion for Application No. PCT/US2018/017762, dated Jun. 7, 2018, 12 pages.
Hu, Ying et al., "Detection of Analysis of DNA Recapture Through a Solid-State Nanopore," Chinese Science Bulletin, Oct. 2014, vol. 59, No. 35, p. 4953-4959.

\* cited by examiner

FIG. 1

| CELL-BLOCK 0 | CELL-BLOCK 1 | CELL-BLOCK 2 | CELL-BLOCK 3 |
|---|---|---|---|
| CELL-BLOCK 4 | CELL-BLOCK 5 | CELL-BLOCK 6 | CELL-BLOCK 7 |
| CELL-BLOCK 8 | CELL-BLOCK 9 | CELL-BLOCK 10 | CELL-BLOCK 11 |
| CELL-BLOCK 12 | CELL-BLOCK 13 | CELL-BLOCK 14 | CELL-BLOCK 15 |

INTEGRATED CIRCUITS FOR ANALYZING BIOLOGICAL SYSTEMS

This application claims the benefit under 35 U.S.C. § 119(e) of U.S. Provisional Application No. 62/675,517 filed on May 23, 2018, which is incorporated by reference in its entirety.

FIELD

The present disclosure relates to integrated circuits for sensing biological molecules. The integrated circuits can be used to measure the impedance of a biological sample under test. The integrated circuits can be used to sequence polynucleotides using a cell array.

BACKGROUND

Platforms for measuring the properties of biological molecules can include large arrays of individual cells that facilitate high throughput and parallel processing and analysis. Such arrays can be used, for example, in sequencing of polynucleotides and proteins. To accommodate fast measurement times, reduce power consumption, and achieve highly accurate and sensitive measurement, the measurement circuitry can be integrated with the cell array used to process the biological samples. Circuits for improving the accuracy, sensitivity and speed of the measurements is desired.

SUMMARY

According to the present invention, integrated circuits are provided comprising: a cell array comprising a plurality of measurement cells, wherein each of the plurality of measurement cells comprises a sensing circuit configured to measure the impedance of a biological sample under test, wherein the sensing circuit comprises multiple inputs and an output; a row access logic circuit operatively connected to the input of each of the plurality of measurement cells and configured to select rows of the cell array; a cell write logic circuit operatively connected to the input of another of the plurality of measurement cells; an analog multiplexer operatively connected to the output of each of the plurality of measurement cells; a column amplifier circuit operatively connected to the analog multiplexer; an analog to digital converter operatively connected to the column amplifier; a multiplexer-FIFO buffer operatively connected to the analog-to-digital converter; and an external interface operatively connected to the multiplexer-FIFO buffer.

According to the present invention, biosensing circuits comprise: a measurement cell, wherein the measurement cell comprises: a cell volume; a counter electrode (CE) disposed within a first portion of the cell volume; and a working electrode (WE) disposed within a second portion of the cell volume; and a measurement circuit, wherein the measurement circuit comprises: a control voltage input; a reset voltage input; a WE input, wherein the WE input is interconnected to the WE; and an output.

According to the present invention, measurement circuits comprise a biosensing circuit according to the present invention.

According to the present invention, molecular sensing apparatus comprise a biosensing circuit according to the present invention.

According to the present invention, methods of sensing a molecule comprise: initiating the biosensing circuit according to the present invention by applying a control voltage; resetting the biosensing circuit by applying a reset voltage to the output; applying an AC waveform to CE; and sampling the AC waveform at the output.

According to the present invention, methods of sensing a biomolecule, comprise applying a transition voltage to CE of the biosensing circuit according to the present invention; resetting the biosensing circuit by applying a reset voltage to the output; and sampling the voltage of the AC waveform.

According the present invention, methods of sensing a biological sample under test comprising using an integrated circuit provided by the present invention.

BRIEF DESCRIPTION OF THE DRAWINGS

Those skilled in the art will understand that the drawings described herein are for illustration purposes only. The drawings are not intended to limit the scope of the present disclosure.

DETAILED DESCRIPTION

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of about 1 and the recited maximum value of about 10, that is, having a minimum value equal to or greater than about 1 and a maximum value of equal to or less than about 10. Also, in this application, the use of "or" means "and/or" unless specifically stated otherwise, even though "and/or" may be explicitly used in certain instances.

"Sample under test" refers to a biological material such as a polynucleotide or a protein.

"Polynucleotide" refers to a polymeric form of nucleotides of any length, either deoxyribonucleotides or ribonucleotides, or analogs thereof. Polynucleotides can have any three-dimensional structure, and may perform any function, known or unknown. Examples of polynucleotides:

include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide can be further modified after polymerization, such as by conjugation with a labeling component.

Reference is now made to certain integrated circuits provided the present invention. The disclosed integrated circuits are not intended to be limiting of the claims. To the contrary, the claims are intended to cover all alternatives, modifications, and equivalents.

Biosensor integrated circuits are designed to measure one or more properties of a biological material within individual measurement cells of a cell array. A cell array can comprise, for example, from 1,000 to 10,000,000 individual cells, from 2,000 to 7,000,000 individual cells, from 500,000 to 5,000,000 individual cells, or from 2,000 to 2,000,000 measurements cells, such as 1,048,576 cells. A bio-sensor integrated circuit can be configured to measure the impedance of a biological material within a measurement cell in the cell array, digitize the measured impedance, and output the digitized results.

A biological molecule can include, for example, a macromolecule such as a polynucleotide or a protein. A polynucleotide can comprise genomic DNA, genomic cDNA, cell free DNA, cell free cDNA, or a combination of any of the foregoing. A polynucleotide can include cell-free DNA, circulating tumor DNA, genomic DNA, and DNA from formalin fixed, and paraffin embedded samples. A sample can comprise any suitable DNA and/or cDNA sample such as for example, urine, stool, blood, saliva, tissue, biopsy, bodily fluid, or tumor cells. A polynucleotide sample can be derived from any suitable source. For example, a sample can be obtained from a patient, from an animal, from a plant, or from the environment such as, for example, a naturally occurring or artificial atmosphere, a water system, soil, an atmospheric pathogen collection system, a sub-surface sediment, groundwater, or a sewage treatment plant. Polynucleotides from a sample may include one more different polynucleotides, such as, for example, DNA, RNA, ribosomal RNA (rRNA), transfer RNA (tRNA), micro RNA (miRNA), messenger RNA (mRNA), fragments of any of foregoing, or combinations of any of the foregoing. A sample can comprise DNA. A sample can comprise genomic DNA. A sample can comprise mitochondrial DNA, chloroplast DNA, plasmid DNA, bacterial artificial chromosomes, yeast artificial chromosomes, oligonucleotide tags, or a combination of any of the foregoing.

A biosensor integrated circuit provided by the present disclosure can be integrated into a platform comprising an array of measurement cells.

Figure 1:
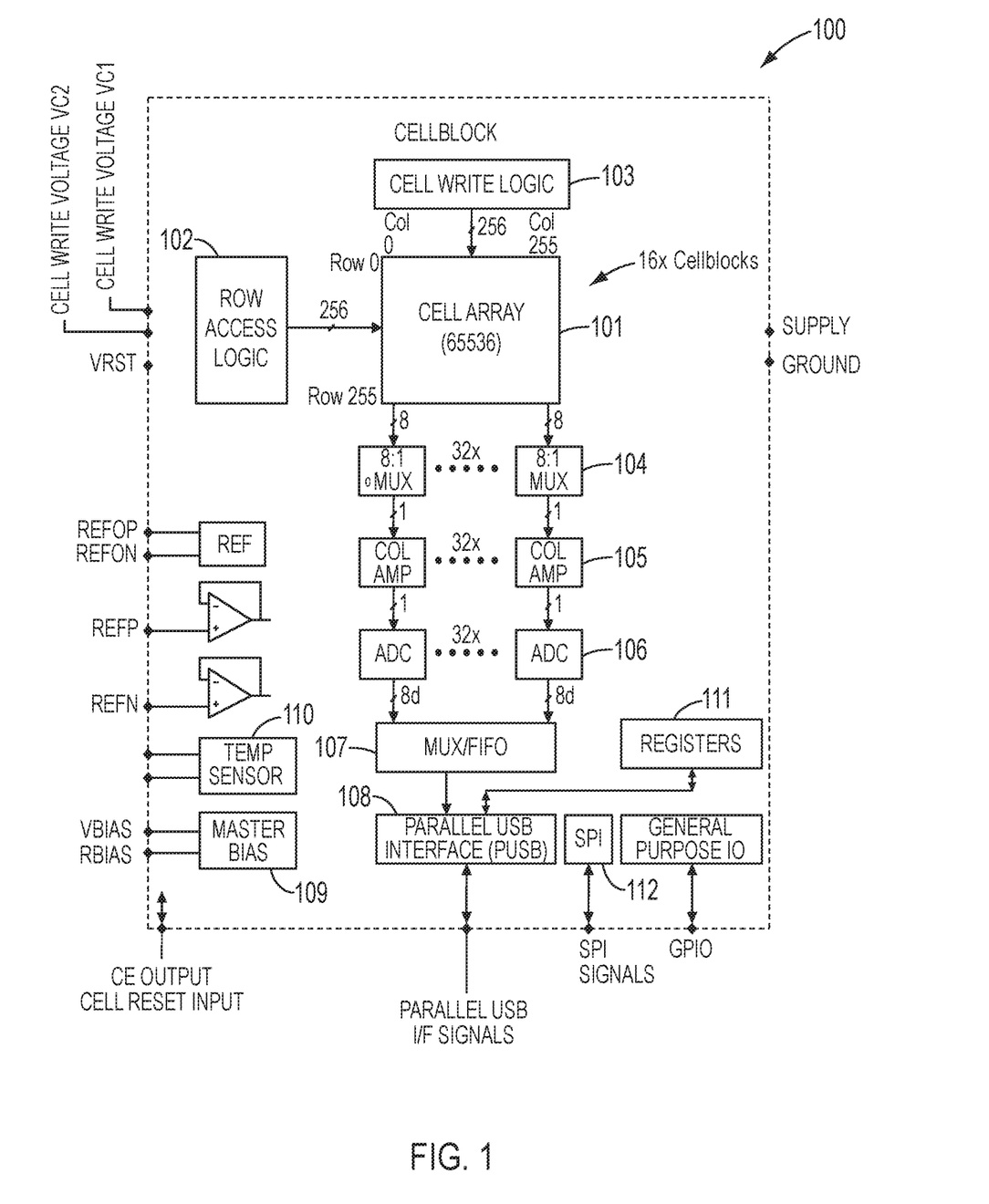
FIG. 1 shows a schematic of an example of an integrated circuit provided by the present disclosure

A block diagram of an example of a biosensor integrated circuit is shown in FIG. 1. The integrated circuit 100 shown in FIG. 1 includes a cell array 101, row access logic 102, cell write logic 103, column analog multiplexers 104, column amplifiers 105, analog to digital converters (ADC) 106, mux/FIFO buffer 107, parallel USB interface 108, master bias 109, and temperature sensor 110.

Cell array 101 comprises a plurality of individual measurement cells. Each measurement cell can comprise a sensing circuit configured to measure an impedance of a biological material such as a polynucleotide, a portion of a biological material such as a nucleic acid, or a tag associated with the biological material. The sensing circuit can be coupled to a microfluidic sample processing system.

To increase the read/conversion time of the measurement cells, a cell array can be partitioned into smaller cell arrays, referred to as cell blocks. For example, a cell array 101 comprising 1,048,576 individual cells arranged in 1,024 columns and 1,024 rows, can be partitioned into 16 cell blocks, with each cell block comprising 65,536 individual cells.

For example, each cell block can comprise 65,536 cells consisting of 256 rows and 256 columns, associated row access logic for each cell block, thirty-two (32) 8:1 analog multiplexers, thirty-two (32) column amplifiers, and thirty-two (32) ADCs.

Cell write logic 103 is electrically connected to each of the individual measurement cells and in conjunction with the row access logic 102, determines the timing when the sensing circuit of a measurement cell is accessed and the sensed signal, such as the impedance, is read and sent to the detection circuitry. The detection circuitry can comprise column analog multiplexers 104, column amplifiers 105, and analog to digital converters (ADC) 106.

Cell write logic enables the selection of two possible voltages for each individual cell. The two possible voltages are presented on two pins to the chip. The selected voltage can be applied to the cell circuit, and depending on the value, can serve to: (1) enable the cell, (2) disable the cell, or (3) enable the cell and determine the voltage that is forced across the sample under test.

Each cell block can be electrically independent of each of the other cell blocks.

Figure 2:
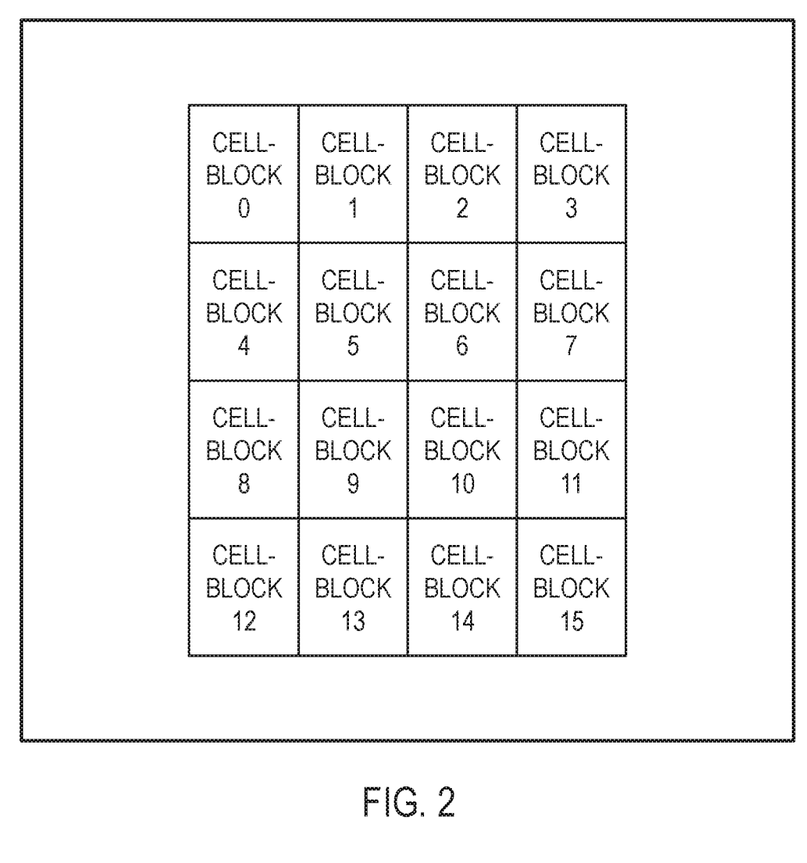
FIG. 2 shows an example of a cell block partitioning in an integrated circuit provided by the present disclosure.

An example of the partitioning of the cell array partitioned into 16 cell blocks (cell blocks 0 to 15) is shown in FIG. 2.

The following description refers to a cell array having a total of 1,048,576 individual cells arranged in 1,024 columns and 1,024 rows, can be partitioned into 16 cell blocks, with each cell block comprising 65,536 individual cells having 256 columns and 256 rows.

To access a cell within a cell block, each of the measurement cells within a row are simultaneously accessed by the row access logic. The analog voltage of each of the 256 cells within a row is output to an 8:1 analog multiplexer. The sensing circuit of a measurement cell forces a voltage across a sample under test such as a biological molecule. Different voltages can be applied across the sample under test and the selection of which voltage to apply can be determined by the cell write logic circuit 103. The analog voltage is proportional to the impedance of the measurement cell. As the analog multiplexer sequentially accesses each of the columns of the cell array, the analog voltage from the sensing circuit of each cell within the column is provided to the associated column amplifier 105. The column amplifier drives the line capacitance of the column and presents the analog voltage to an ADC, such as an 8-bit ADC, for conversion to a digital output, such as an 8-bit digital signal. For each row, the ADC performs eight consecutive analog-to-digital conversions, one for each of the eight accessed columns. Each row access produces 256 8-bit digital outputs from each of the accessed cells in the accessed row. These 8-bit digital outputs are then sent to a buffer (mux/FIFO), and subsequently to a suitable interconnection interface such as a parallel USB interface to be output to an external device. After each of the cells within a row is accessed, read, and output, the subsequent row can be accessed, and the process repeated until each measurement cell of the cell array is read, converted, and output.

A sensing circuit can include, for example, three (3) analog inputs (VC1, VC2, and VRST) and two digital inputs. A sensing circuit can comprise multiple inputs.

FIG. 2 shows details of an example of a physical arrangement of cell blocks of an integrated circuit device. The device includes a cell array partitioned into 16 cell blocks including cellblock 0 to cell block 15. Row 0 is physically located on the top of each cell block and row 255 at the bottom of each cell block. Column 0 is physically located on the left side of each cellblock and column 255 is physically located at the right side of each cell block. Cell block 0 is physically located on the top right of the cell array and cell block 15 on the bottom right of the cell array.

To induce a current through the sample under test, a voltage can be applied across the sample under test. The sample under test voltage is sourced to the integrated circuit on either pins VC1 and VC2 shown in FIG. 1. The selected sample under test voltage can be determined by the cell write logic and the row access logic.

Several device configuration settings and status outputs can be selected and set by a user. These configuration settings and status outputs can be stored in internal registers (111 in FIG. 1). The internal registers can be written and read out via an external interface such as a parallel USB interface 108 or using a serial peripheral interface bus (SPI) 112.

The integrated circuit can include a master bias 109, which generates bias currents and voltages for the internal circuits. The bias currents and voltages can be provided to the master bias by an external source.

The integrated circuit can include an internal temperature sensor. The output of the internal temperature sensor can be used to monitor the integrated circuit temperature and control an external cooling device configured to maintain the integrated circuit at a pre-determined temperature.

Each measurement cell of a cell array comprises a sensing circuit for measuring an impedance of a biological material the cell. The biological material such as a polynucleotide is also referred to as the sample under test.

A biosensor circuit can be configured in two ways. In a first configuration, a sensing circuit can comprise a pre-charged capacitor, which is discharged by the impedance of the sample under test. In this configuration, the sensing circuit can employ a reduced number of transistors and can utilize replica biasing for accurate voltage control.

To detect the impedance of the sample under test, a current is generated that is proportional to the impedance of the sample under test. The generated current discharges the pre-charged capacitor, and the resultant voltage is proportional to the impedance of sample under test impedance. This current is generated by imposing a fixed voltage across the sample under test, thus producing a constant current that is a function of the impedance of the sample under test. The voltage that is imposed across the sample under test is created indirectly through a replica bias circuit.

In a second configuration, a current mirror circuit can be used in which the impedance of the sample under test is converted to a current, the current amplified, and the amplified current converted to a voltage using a summing amplifier. Any suitable current mirror circuit can be used.

The column amplifiers buffer each measurement cell and drive the capacitance of each respective column. Each measurement cell is sequentially connected to its associated column amplifier via a multiplexer. This cell voltage is then input to the column amplifier and sent to the ADC for conversion to a digital output. The column multiplexers and column amplifiers can be separate circuits.

Alternatively, the column multiplexers and the column amplifiers can be integrated into a single circuit. Integrating the column multiplexers and amplifiers reduces the physical area used for the two functions and reduces power consumption.

The impedance of the sample under test is typically small. To convert the impedance to a voltage that can be easily detected, a pre-charged capacitor is discharged for a given time by the sample under test impedance to create a voltage that is proportional to the sample under test impedance and large enough for detection. This node that has the capacitor is the cell voltage output. However, the cell voltage output cannot be switched to the column line because the capacitance of the column line would redistribute with the cell capacitor capacitance and reduce the signal to a small value that might not be able to be detected reliably. For this reason, simply placing a multiplexer between the cell output and column amplifier will not give accurate readings. A traditional approach would be to have one column amplifier per column, and place a few of the column amplifiers in each cell to buffer the cell output from the column line capacitance. Column amplifiers can be placed within the cell to buffer the output voltage. However, to reduce the area of the integrated circuit and to minimize power consumption it is desirable that there not be one column amplifier per column. To address this issue a multiplexer can be incorporated into the column amplifier such that the cell output voltage is buffered by the few column amplifiers in each cell but has the multiplexing function built into the column amplifier. Thus, using an 8:1 imbedded multiplexer, 1 column amplifier per 8 columns can be used, thereby reducing the area and power consumption.

In a typical operation, the sensing circuit measures the impedance of the sample under test in the measurement cell. However, under certain conditions, an ancillary capacitance can arise between the sensing circuit and the sample under test. Such capacitance can be caused, for example, by chemical reactions external to the cell sensing circuit within the measurement cell. This ancillary capacitance prevents or interferes with the flow of DC current through the sample under test.

To circumvent the effects of this ancillary capacitance and allow accurate and sensitive measurement of the sample under test, an integrated circuit provided by the present disclosure can include AC modes of sensing the impedance of the sample under test. An AC sensing mode can be integrated into the integrated circuit or can be generated external to the integrated circuit.

For example, using an AC mode test algorithm a low frequency AC signal can be applied across the sample under test. The impedance of the sample under test will be a function of the rise and fall time of the AC signal through the sample under test. The rise and fall times of the applied AC signal can be measured at random intervals to measure the impedance of the sample. A low frequency AC signal refers to an AC waveform such as a square waveform having a characteristic frequency, for example, from 10 Hz to 1000 Hz.

Alternative AC modes of operation can provide improved measurement accuracy.

In an AC generation mode, a low frequency AC waveform can be applied to the sample under test. The low frequency AC waveform generator circuit can be external to the integrated circuit or can be incorporated into the integrated circuit. A cell reset signal generator can also be incorporated into the integrated circuit. The AC waveform and the cell reset signal can be temporally synchronized and applied globally to each of the measurement cells of the cell array. Synchronization of the AC waveform and the cell reset signal facilitates fast and accurate measurement of the rise and fall times of the AC waveform generated by the sample under test. Furthermore, the AC waveform can be interrogated at programmable intervals, which can increase the dynamic range (sensitivity) of the AC waveform measurement.

In an AC mode of operation, the cell reset and AC waveform occur in a precise, synchronized sequence. In a standard measurement method, the cell reset and AC waveform can be asynchronous to each other because the reset is generated on the chip and the AC waveform is generated external to the chip. In measurement methods provided by the present disclosure, the cell reset and AC waveform are synchronized. The synchronization can be accomplished by generating the cell reset and AC waveform either internally or externally. If generated internally, the cell reset and AC waveform are generated on the chip. Alternatively, the cell reset and AC waveform can be generated externally and input to the chip.

A pre-determined cell reset time can be used to establish when to begin sampling the AC measurement signal. With a non-pre-determined cell reset time, the reset time is random and AC measurement can begin at any point in time resulting in many invalid measurements. By setting a pre-determined reset time and reset voltage of the cell, AC measurements will be valid and more accurate.

Rather than generate the AC waveform and the cell reset signal internally, i.e. the AC waveform and cell reset generators are incorporated into the integrated circuit, the AC waveform can be generated externally and input to the integrated circuit. This mode allows for more flexibility in defining the characteristics of the AC waveform. When the AC waveform is generated on the chip the AC waveform can be a square wave. An external AC waveform can be generated an input to the chip. Generating the AC waveform externally provides the ability to apply other waveforms such as sinusoidal or triangular waveforms.

As another example, rather than applying a single AC waveform to a measurement cell, two or more AC waveforms, where each of the two or more AC waveforms has a different characteristic frequency, can be applied to the measurement cell. The two or more AC waveforms can be generated internally, externally, or a combination thereof. The measured peak voltage at each frequency will depend on the impedance of the measurement cell and the sample under test. By analyzing the peak voltage at the different frequency, the ancillary capacitance of the measurement cell can be decoupled from the impedance of the sample under test.

In a standard method, a square wave is imposed across the sample under test, and the resulting rise and fall times measured at the cell output are proportional to the impedance of the sample under test and the internal capacitor. In methods provided by the present disclosure, a sinewave is imposed across the sample under test, and the combination of the impedance of the sample under test and the internal cell capacitor functions as a low pass filter, which attenuates the sinewave forced on the sample under test. The attenuation of the sinewave is proportional to the impedance of the sample under test.

Another method of making an AC measurement is to reset the measurement circuit and pulse the AC waveform. In this mode, the measurement cell capacitor can be first reset to a fixed voltage and then at the end of the reset period, an AC waveform is applied to the sample under test, and the voltage on the measurement cell capacitor is measured.

The waveform shape and voltage on the measurement cell capacitor is a function of the impedance of the sample under test, the capacitance of the internal cell capacitor, and the delay between the rise/fall of the AC waveform and the time the voltage on the internal capacitor is measured.

The voltage on the internal cell capacitor can be measured on the positive edge of AC waveform, the negative edge of AC waveform, or on both the positive and negative edges of the AC waveform. When the measurement is made on both edges the measured voltages can be subtracted to account for systematic errors in the system/circuit.

Another method of making an AC measurement is to pulse, the AC waveform followed by resetting the measurement circuit. In this configuration the pulsed AC waveform is first applied to the sample under test and then the measurement cell capacitor can be reset to a fixed voltage. At the end of the reset period, the voltage across the measurement cell capacitor is measured.

The shape of the waveform at the measurement cell capacitor is a function of the impedance of the sample under test and the capacitance of the internal capacitor.

The voltage across the measurement cell capacitor can be measured on the positive edge of AC waveform, the negative edge of AC waveform, or on both the positive and negative edges of the AC waveform. When the measurement is made on both edges, the measured voltages can be subtracted to account for systematic errors in the system/circuit.

The voltage across the capacitor can be measured at one or more points during the rise and/or fall of the AC waveform. Taking multiple measurements can increase accuracy and sensitivity using signal averaging methods.

Cells within a cell block can be sequentially accessed by column and by row. After each of the 256 cells of a row are accessed and the row is reset. Because the rows are read sequentially, a row will not be accessed until after each of the other 255 rows in a cell block are also read. As a result, the capacitor coupled to each cell discharges by the sample under test for a duration equal to the row read time multiplied by 256, referred to as the cell cycle time.

Under certain conditions, the cell capacitor can discharge to zero faster than the cell cycle time. In this situation, to obtain valid impedance measurements, the capacitor discharge time needs to be decreased (e.g., the discharge rate reduced) to prevent the capacitor from totally discharging to zero before the measurement cell can be accessed and interrogated.

To prevent the capacitor from discharging to zero, the time between row reset signals can be reduced to less than 256 row read times. Accordingly, the integrated circuit can incorporate the ability to program the interval between row resets from 1 to 256 row read times. This allows a user to adjust the row reset rate to match the impedance of the sample under test without having to modify the chip speed or clocks.

This feature can be used in AC mode to sample the waveform at a specific time(s) to measure the exponential component of the waveform.

Rows in a cellblock can be accessed and read sequentially, such as from row 0 to row 255.

Alternatively, rows can be accessed non-sequentially. For example, certain rows can be omitted from the read process and/or certain rows can be accessed in a non-sequential order or in a random order. To accomplish this an integrated circuit provided by the present disclosure can incorporate the ability to select the sequence in which rows are accessed and/or which rows within a cellblock are accessed.

Methods provided by the present disclosure comprise using the integrated circuits disclosed herein to sense biological molecules.

Methods of sensing a molecule can comprise applying a control voltage to the measurement circuit resetting the measurement circuit by applying a reset voltage, applying an AC waveform to the measurement circuit; and sampling the AC waveform.

Methods of sensing a molecule can comprise applying an AC waveform to the measurement circuit, applying a reset voltage to the measurement circuit by applying a reset voltage, and sampling the AC waveform.

Applying an AC waveform can comprise applying a pulsed AC waveform.

Sampling the AC waveform can comprise sampling the risetime of the AC waveform, sampling the fall time of the AC waveform, or sampling both the rise time and the fall time of the AC waveform. The AC waveform can be sampled at one time point on the rise time and/or fall time of the AC waveform AC waveform or at multiple time points on the rise time and/or fall time of the AC waveform.

In this way, the read time of a cell block can be adjusted to accommodate the discharge rate of the capacitor. Furthermore, rows having compromised measurement cells can be eliminated from the read sequence, and thereby increase the overall throughput of the device.

ASPECTS OF INVENTION

Aspect 1. An integrated circuit comprising: a cell array comprising a plurality of measurement cells, wherein each of the plurality of measurement cells comprises a sensing circuit configured to measure the impedance of a biological sample under test, wherein the sensing circuit comprises multiple inputs and an output; a row access logic circuit operatively connected to the input of each of the plurality of measurement cells and configured to select rows of the cell array; a cell write logic circuit operatively connected to the input of another of the plurality of measurement cells; an analog multiplexer operatively connected to the output of each of the plurality of measurement cells; a column amplifier circuit operatively connected to the analog multiplexer; an analog to digital converter operatively connected to the column amplifier; a multiplexer-FIFO buffer operatively connected to the analog-to-digital converter; and an external interface operatively connected to the multiplexer-FIFO buffer.

Aspect 2. The integrated circuit of aspect 1, wherein the cell array comprises from 1,000 to 10,000,000 measurement cells.

Aspect 3. The integrated circuit of any one of aspects 1 to 2, wherein the cell array comprises a plurality of cell blocks, wherein each of the plurality of cell blocks comprises a plurality of the measurement cells.

Aspect 4. The integrated circuit of 3, wherein each of the plurality of cell blocks comprises from 1,000 to 10,000,000 measurement cells.

Aspect 5. The integrated circuit of 3, wherein the cell array comprises 1,048,576 measurement cells; 16 cell blocks, and each of the cell blocks comprises 65,536 measurement cells.

Aspect 6. The integrated circuit of any one of aspects 3 to 5, wherein each of the measurement cells within a cell block is connected to 1 of 32 8:1 multiplexers.

Aspect 7. The integrated circuit of any one of aspects 3 to 6, wherein each of the plurality of cell blocks is configured to operate independently of each of the other cell blocks.

Aspect 8. The integrated circuit of any one of aspects 1 to 7, wherein the sensing circuit is configured to measure an impedance of a sample under test within the respective measurement cell.

Aspect 9. The integrated circuit of any one of aspects 1 to 8, wherein the sensing circuit comprises: a pre-charged capacitor configured to be discharged by the impedance of a sample under test within the respective measurement cell; and a replica bias voltage regulator configured to impose a voltage across the sample under test.

Aspect 10. The integrated circuit of any one of aspects 1 to 9, wherein the sensing circuit comprises a current mirror circuit.

Aspect 11. The integrated circuit of any one of aspects 1 to 10, wherein the current mirror is configured to: convert the impedance of the sample under test to a current; amplify the current; and convert the amplified current to a voltage using a summing amplifier.

Aspect 12. The integrated circuit of any one of aspects 1 to 11, wherein the analog multiplexer and the column amplifier are integrated and each measurement cell is coupled to a multiplexer-amplifier.

Aspect 13. The integrated circuit of any one of aspects 1 to 12, wherein the sensing circuit comprises an AC generation circuit configured to generate a low frequency AC waveform; and a capacitor reset circuit configured to generate a capacitor reset signal; wherein the low frequency AC waveform and the capacitor reset signal are temporally synchronized.

Aspect 14. The integrated circuit of any one of aspects 1 to 13, wherein the low frequency waveform comprises a frequency from 10 Hz to 1,000 Hz.

Aspect 15. The integrated circuit of aspect 14, wherein the impedance of the sample under test is a function of the rise and fall time of the AC waveform through the sample under test.

Aspect 16. The integrated circuit of any one of aspects 14 to 15, wherein the sensing circuit is configured to allow measurement of the rise and fall time of the AC waveform at selected times.

Aspect 17. The integrated circuit of any one of aspects 14 to 16, wherein, the AC generation circuit is configured to generate an AC waveform characterized by two different frequencies.

Aspect 18. The integrated circuit of aspects 1 to 17, wherein the measurement cell sensing circuit comprises an external AC generation circuit configured to generate one or more low frequency AC waveforms; and an external measurement cell capacitor reset circuit configured to generate a measurement cell capacitor reset signal, wherein the low frequency AC waveform and the measurement cell capacitor reset signal are synchronized.

Aspect 19. The integrated circuit of aspect 18, wherein the measurement cell capacitor reset circuit is configured to reset the measurement cell capacitor to a fixed voltage.

Aspect 20. The integrated circuit of any one of aspects 18 to 19, wherein the low frequency AC waveform comprises a pulsed AC waveform.

Aspect 21. The integrated circuit of any one of aspects 18 to 20, further comprising a measurement circuit configured to measure the voltage across the measurement cell capacitor during the positive edge of the pulsed AC waveform, during the negative edge of the pulsed AC waveform, or during both the negative edge of the pulsed AC waveform and the negative edge of the pulsed AC waveform.

Aspect 22. The integrated circuit of aspect 21, wherein the sensing circuit is configured to apply the measurement cell capacitor reset signal, apply the AC waveform, and measure the voltage of the AC waveform across the measurement cell capacitor.

Aspect 23. The integrated circuit of aspect 21, wherein the sensing circuit is configured to apply the AC waveform, apply the measurement cell capacitor reset signal, and measure the voltage of the AC waveform across the measurement cell capacitor.

Aspect 24. The integrated circuit of any one of aspects 21 to 23, wherein the sensing circuit is configured to make multiple measurements of the AC waveform.

Aspect 25. The integrated circuit of any one of aspects 1 to 24, comprising a read time circuit configured to set a duration between a time of capacitor reset and a time of reading a measurement cell.

Aspect 26. The integrated circuit of aspect 25, wherein, the duration is from 1 to 256 row read times.

Aspect 27. The integrated circuit of any one of aspects 25 to 26, wherein the duration is selected to match the impedance of the sample under test.

Aspect 28. The integrated circuit of any one of aspects 1 to 27, comprising a row read circuit configured to read rows within a cell block non-sequentially, wherein the row read circuit is connected to the sensing circuit.

Aspect 29. The integrated circuit of aspect 28, wherein the row read circuit is programmable by a user.

Aspect 30. The integrated circuit of any one of aspects 28 to 29, wherein the row read circuit is configured to independently enable or disable each of the rows.

Aspect 31. A method of sensing a biological sample under test comprising using the integrated circuit of any one of claims 1 to 30.

It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

What is claimed is:

1. An integrated circuit comprising:
    a cell array comprising a plurality of measurement cells, wherein each of the plurality of measurement cells comprises a sensing circuit configured to measure the impedance of a biological sample under test, wherein the sensing circuit comprises:
        multiple inputs and an output;
        a pre-charged measurement cell capacitor configured to be discharged by the impedance of a sample under test within the respective measurement cell; and
        a replica bias voltage regulator configured to impose a voltage across the sample under test;
    a row access logic circuit operatively connected to the input of each of the plurality of measurement cells and configured to select rows of the cell array;
    a cell write logic circuit operatively connected to the input of another of the plurality of measurement cells;
    an analog multiplexer operatively connected to the output of each of the plurality of measurement cells;
    a column amplifier circuit operatively connected to the analog multiplexer;
    an analog to digital converter operatively connected to the column amplifier;
    a multiplexer-FIFO buffer operatively connected to the analog to digital converter; and
    an external interface operatively connected to the multiplexer-FIFO buffer.

2. The integrated circuit of claim 1, wherein the cell array comprises a plurality of cell blocks, wherein each of the plurality of cell blocks comprises a plurality of the measurement cells.

3. The integrated circuit of claim 2, wherein each of the measurement cells within a cell block is connected to 1 of 32 8:1 multiplexers.

4. The integrated circuit of claim 2, wherein each of the plurality of cell blocks is configured to operate independently of each of the other cell blocks.

5. The integrated circuit of claim 1, wherein the analog multiplexer and the column amplifier are integrated and each measurement cell is coupled to a multiplexer-amplifier.

6. The integrated circuit of claim 1, comprising a read time circuit configured to set a duration between a time of measurement cell capacitor reset and a time of reading a measurement cell.

7. The integrated circuit of claim 6, wherein the duration is selected to match the impedance of the sample under test.

8. The integrated circuit of claim 1, comprising a row read circuit configured to read rows within a cell block non-sequentially, wherein the row read circuit is connected to the sensing circuit.

9. The integrated circuit of claim 8, wherein the row read circuit is configured to independently enable or disable each of the rows.

10. A method of sensing a biological sample under test comprising using the integrated circuit of claim 1.

11. An integrated circuit comprising:
    a cell array comprising a plurality of measurement cells, wherein each of the plurality of measurement cells comprises a sensing circuit configured to measure the impedance of a biological sample under test, wherein the sensing circuit comprises:
        multiple inputs and an output; and
        a current mirror circuit, wherein the current mirror is configured to:
            convert the impedance of the sample under test to a current;
            amplify the current; and
            convert the amplified current to a voltage using a summing amplifier;
    a row access logic circuit operatively connected to the input of each of the plurality of measurement cells and configured to select rows of the cell array;
    a cell write logic circuit operatively connected to the input of another of the plurality of measurement cells;
    an analog multiplexer operatively connected to the output of each of the plurality of measurement cells;
    a column amplifier circuit operatively connected to the analog multiplexer;
    an analog to digital converter operatively connected to the column amplifier;
    a multiplexer-FIFO buffer operatively connected to the analog to digital converter; and an external interface operatively connected to the multiplexer-FIFO buffer.

12. A method of sensing a biological sample under test comprising using the integrated circuit of claim 11.

13. An integrated circuit comprising:
a cell array comprising a plurality of measurement cells, wherein each of the plurality of measurement cells comprises a sensing circuit configured to measure the impedance of a biological sample under test, wherein the sensing circuit comprises:
multiple inputs and an output;
an AC generation circuit configured to generate a low frequency AC waveform; and
a measurement cell capacitor reset circuit configured to generate a measurement cell capacitor reset signal;
wherein the low frequency AC waveform and the measurement cell capacitor reset signal are temporally synchronized;
a row access logic circuit operatively connected to the input of each of the plurality of measurement cells and configured to select rows of the cell array;
a cell write logic circuit operatively connected to the input of another of the plurality of measurement cells;
an analog multiplexer operatively connected to the output of each of the plurality of measurement cells;
a column amplifier circuit operatively connected to the analog multiplexer;
an analog to digital converter operatively connected to the column amplifier;
a multiplexer-FIFO buffer operatively connected to the analog to digital converter; and
an external interface operatively connected to the multiplexer-FIFO buffer.

14. The integrated circuit of claim 13, wherein the impedance of the sample under test is a function of the rise and fall time of the AC waveform through the sample under test.

15. The integrated circuit of claim 13, wherein the sensing circuit is configured to allow measurement of the rise and fall time of the AC waveform at selected times.

16. The integrated circuit of claim 13, wherein the AC generation circuit is configured to generate an AC waveform characterized by two different frequencies.

17. A method of sensing a biological sample under test comprising using the integrated circuit of claim 13.

18. An integrated circuit comprising:
a cell array comprising a plurality of measurement cells, wherein each of the plurality of measurement cells comprises a sensing circuit configured to measure the impedance of a biological sample under test, wherein the sensing circuit comprises:
multiple inputs and an output;
an external AC generation circuit configured to generate one or more low frequency AC waveforms; and
an external measurement cell capacitor reset circuit configured to generate a measurement cell capacitor reset signal, wherein the low frequency AC waveform and the measurement cell capacitor reset signal are synchronized;
a row access logic circuit operatively connected to the input of each of the plurality of measurement cells and configured to select rows of the cell array;
a cell write logic circuit operatively connected to the input of another of the plurality of measurement cells;
an analog multiplexer operatively connected to the output of each of the plurality of measurement cells;
a column amplifier circuit operatively connected to the analog multiplexer;
an analog to digital converter operatively connected to the column amplifier;
a multiplexer-FIFO buffer operatively connected to the analog to digital converter; and
an external interface operatively connected to the multiplexer-FIFO buffer.

19. The integrated circuit of claim 18, wherein the low frequency AC waveform comprises a pulsed AC waveform.

20. The integrated circuit of claim 18, further comprising a measurement circuit configured to measure the voltage across the measurement cell capacitor during the positive edge of the pulsed AC waveform, during the negative edge of the pulsed AC waveform, or during both the negative edge of the pulsed AC waveform and the negative edge of the pulsed AC waveform.

21. The integrated circuit of claim 20, wherein the sensing circuit is configured to make multiple measurements of the AC waveform.

22. A method of sensing a biological sample under test comprising using the integrated circuit of claim 18.

* * * * *